United States Patent [19]
Zimmermann et al.

[11] Patent Number: 5,698,541
[45] Date of Patent: Dec. 16, 1997

[54] 2,4-DIPHOSPHONOGLUTARIC ACID DERIVATIVES, PROCESSES FOR THEIR PRODUCTION AND PHARMACEUTICAL AGENTS CONTAINING THESE COMPOUNDS

[75] Inventors: Gerd Zimmermann, Mannheim; Angelika Esswein, Singen; Christos Tsaklakidis, Weinheim; Frieder Bauss, Neuhofen, all of Germany

[73] Assignee: Boehringer Mannheim GmbH, Mannheim, Germany

[21] Appl. No.: 714,076

[22] PCT Filed: Mar. 22, 1995

[86] PCT No.: PCT/EP95/01062

§ 371 Date: Sep. 25, 1996

§ 102(e) Date: Sep. 25, 1996

[87] PCT Pub. No.: WO95/26358

PCT Pub. Date: Oct. 5, 1995

[30] Foreign Application Priority Data

Mar. 26, 1994 [DE] Germany ............... 44 10 601.7

[51] Int. Cl.$^6$ ............... A61K 31/66; C07F 9/38; C07F 9/40
[52] U.S. Cl. ............... 514/129; 514/120; 514/79; 514/88; 514/95; 514/89; 514/99; 514/90; 514/101; 514/94; 514/92; 562/20; 558/156; 558/158; 546/21; 546/22; 546/24; 544/232; 544/243; 548/112; 548/412; 549/5; 549/218; 540/542
[58] Field of Search ............... 562/20; 558/156, 558/158; 546/21, 22, 24; 548/112, 412; 549/5, 218; 540/542; 544/106, 232, 243; 514/129, 130

[56] References Cited

U.S. PATENT DOCUMENTS 3,933,944  1/1976  Moreau .

OTHER PUBLICATIONS

CA95:70845, 1983 Abst of "Diethyl Ester of 2,4 bis(di-ethoxyphosphinyl) pimelic acid" Petrov Zhiobshich Chem. and English translation of article from Plen Pub Corp. 1983.

*Primary Examiner*—C. Warren Ivy
*Assistant Examiner*—Jean F. Vollano
*Attorney, Agent, or Firm*—Nikaido, Marmelstein, Murray & Oram LLP

[57] ABSTRACT

The invention concerns compounds of the general formula I

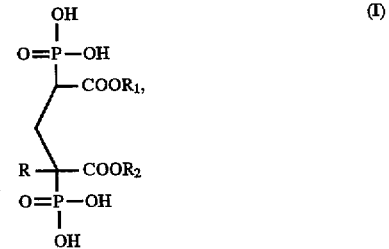

in which

R denotes a lower alkyl which can be substituted if desired by hydroxy, alkoxy, amino, dialkylamino, alkylmercapto, alkylsulfinyl, alkanesulfonyl, cycloalkyl, aryl or a heterocyclic ring, or it denotes lower alkenyl, cycloalkyl, cycloalkenyl, aryl or a heterocyclic ring and $R_1$ and $R_2$ can be, independently of one another, hydrogen, lower alkyl, cycloalkyl, aryl or arylmethyl, their optically active salts as well as their pharmacologically acceptable salts, processes for their production as well as pharmaceutical agents which contain these compounds for treating diseases of calcium metabolism. Moreover the invention concerns compounds of formula II as intermediate products for the production of compounds of formula I.

6 Claims, No Drawings

2,4-DIPHOSPHONOGLUTARIC ACID DERIVATIVES, PROCESSES FOR THEIR PRODUCTION AND PHARMACEUTICAL AGENTS CONTAINING THESE COMPOUNDS

This is the U.S. National Stage application of PCT/EP95/01062 filed Mar. 22, 1995, published as WO 95/26358 on Oct. 5, 1995.

The present invention concerns new 2,4-diphosphonoglutaric acid derivatives, processes for their production and pharmaceutical agents containing these substances.

The hexaethyl ester of 2,4-diphosphonoglutaric acid is described in "Angew. Chemie" 92, 43 (1983) and Can. J. Chem. 60, 840 (1982); J. Org. Chem. 25, 1232 (1960) mentions 2,4-diphosphono-3-phenylglutaric acid hexaethyl ester, however, a pharmacological action of these compounds is not known.

It was now found that 2,4-diphosphonoglutaric acids substituted in the 2 position have an excellent effect on calcium metabolism and are therefore suitable for the broad treatment of disorders of calcium metabolism.

They can be used particularly well in situations where bone synthesis and degradation is disturbed i.e. they are suitable for the treatment of diseases of the skeletal system such as e.g. osteoporosis, Morbus Paget, Morbus Bechterew, paradontoses among others.

Due to these properties they can, however, also be used in the therapy of urolithiasis and to prevent heterotopic ossifications. Furthermore, through their influence on calcium metabolism, they form a basis for the treatment of rheumatoid arthritis, osteoarthritis and degenerative arthrosis. Due to their extremely good affinity to bone mineral, 2,4-diphosphonoglutaric acid and its derivatives are also extremely well-suited to transport pharmacologically active compounds directly to the bones.

The present invention concerns compounds of the general formula I

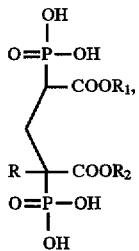

(I)

in which
R denotes lower alkyl which can be substituted if desired by hydroxy, alkoxy, amino, dialkylamino, alkylmercapto, alkylsulfinyl, alkanesulfonyl, cycloalkyl, aryl or by a heterocyclic ring, or it denotes lower alkenyl, cycloalkyl, cycloalkenyl, aryl or a heterocyclic ring and $R_1$ and $R_2$ can each be, independently of one another, hydrogen, lower alkyl, cycloalkyl, aryl or arylmethyl, as well as their pharmacologically acceptable salts.

In all cases lower alkyl is intended to represent a straight-chained or branched $C_1$–$C_6$ alkyl group such as e.g. methyl, ethyl, propyl, isopropyl, butyl, isobutyl, pentyl or hexyl, in particular methyl, ethyl, isopropyl, butyl and hexyl. Lower alkenyl denotes unsaturated residues with 3–6 carbon atoms such as e.g. allyl, but-2-enyl, hexa-2,4-dienyl, but above all allyl.

Cycloalkyl denotes a 3- to 7-membered ring such as a cyclopropyl, cyclobutyl, cyclopentyl, cyclohexyl or cycloheptyl ring, preferably a cyclopentyl and cyclohexyl ring.

Cycloalkenyl is intended to represent an unsaturated 5–7 ring such as a cyclopentenyl, cyclohexenyl and cycloheptenyl ring.

Alkoxy is understood as residues such as a methoxy, ethoxy, propoxy, isopropoxy, butoxy or pentoxy residue, in particular a methoxy, ethoxy, isopropoxy and butoxy residue.

Dialkylamino is intended to represent an amino group with two equal or different $C_1$–$C_5$ alkyl residues such as e.g. dimethylamino, methylpropylamino, methylpentyl-amino, diethylamino or dipropylamino and above all dimethylamino, methylpropylamino and methylpentylamino.

Alkylmercapto, alkylsulfinyl and alkanesulfonyl are preferably understood to mean methylmercapto, methylsulfinyl and methanesulfonyl respectively.

Aryl denotes a phenyl or naphthyl residue which can be substituted once or several times, if desired, by lower alkyl, halogen, hydroxy, alkoxy, amino, dialkylamino, alkylmercapto, alkylsulfinyl, alkanesulfonyl, carboxamido which can be substituted once or twice by lower alkyl, or by carboxyl, alkoxycarbonyl or cyano.

A heterocyclic ring is understood to be a 5- to 7-membered, saturated or unsaturated ring such as e.g. a pyrrolidine, piperidine, azepine, tetrahydrofuran, tetrahydropyran, morpholine, dioxan, furan, thiophene, pyridine, pyrazole, imidazole, thiazole, oxazole, pyrimidine or pyrazine ring, preferably a pyrrolidine, piperidine, morpholine, furan, thiophene, pyridine and imidazole ring, wherein the ring system can be substituted once or several times by halogen, lower alkyl or alkoxy.

Halogen is intended to represent fluorine, chlorine, bromine and iodine, in particular fluorine and chlorine.

Compounds of the general formula I contain at least two asymmetric carbon atoms; therefore optically active compounds of the general formula I are also a subject matter of the present invention.

Compounds of the general formula I are synthesized by well-known processes, preferably by saponifying a compound of the general formula II,

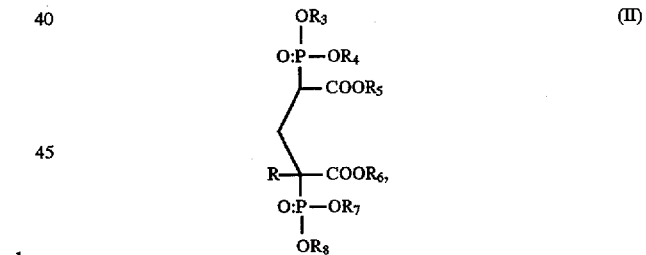

(II)

in which R has the meaning stated above and $R_3$, $R_4$, $R_5$, $R_6$, $R_7$ and $R_8$ each denote, independently of one another, lower alkyl, cycloalkyl, aryl or arylmethyl in such a way that either all ester bonds are hydrolyzed or a partial saponification is achieved by suitable reagents.

A complete saponification of compounds having the general structure II is achieved by boiling with aqueous mineral acids, preferably with 6N hydrochloric acid.

Selective saponification of the phosphonic ester groups can be achieved with halogentrialkylsilanes, preferably with bromotrimethylsilane or iodotrimethylsilane in inert solvents such as dichloromethane at temperatures between −50° C. and +50° C., preferably at 0°–20° C. If benzyl esters are present in the compounds of formula II, these can be selectively cleaved by catalytic hydrogenation e.g. over palladium/carbon.

The compounds of the general formula II are novel and a subject matter of the invention. They can be synthesized a) analogously to the process described in Can. J. Chem. 60, 840 (1982) by reacting a compound with the structure III in which the residues R, $R_6$, $R_7$ and $R_8$ have the aforementioned meaning with a phosphonoacrylic ester of the general formula IV in which $R_3$, $R_4$ and $R_5$ have the aforementioned meaning in the presence of a strong base, preferably sodium hydride in tetrahydrofuran or sodium methylate in methanol,

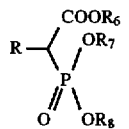

III

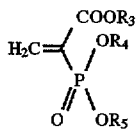

IV or b) in that a compound of the general formula V in which R, $R_5$ and $R_6$ have the aforementioned meaning and X represents a leaving group such as e.g. halogen, preferably bromine or iodine, or it represents a group $—O—SO_2—Z$, in which Z represents methyl or aryl e.g. phenyl or p-nitrophenyl, is reacted with a trialkylphosphite analogous to the process described in "Angew. Chem." 92, 43 (1980).

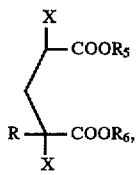

(V)

The compounds of the general formulae III, IV and V have been described or can be synthesized according to analogous processes.

Mixtures of diastereomers of compounds of formula I or their precursors can be separated, provided that at least two asymmetric C atoms are present, by known processes such as crystallization or by chromatographic processes. It is possible to determine the absolute configuration of enantiomers by X-ray structural analysis.

Monoalkali, dialkali or ammonium salts are used above all as pharmacologically acceptable salts which are produced in the usual manner for example by titrating the compounds with inorganic bases such as e.g. sodium or potassium bicarbonate, sodium hydroxide, potassium hydroxide, aqueous ammonia or amines such as e.g. trimethylamine or triethylamine.

The salts are usually purified by precipitating from water/acetone. However, it is also possible to use calcium, magnesium or zinc salts which are usually sparingly soluble in water but are also occasionally readily soluble. These salts can be prepared by allowing a calcium, zinc or magnesium salt such as e.g. calcium carbonate, calcium bicarbonate, calcium hydroxide, calcium chloride, zinc carbonate, zinc bicarbonate, zinc hydroxide, zinc chloride, magnesium carbonate, magnesium bicarbonate, magnesium hydroxide or magnesium chloride to be stirred as an aqueous solution or suspension in a ratio of 1:1 or 2:1 with an aqueous solution or suspension of the 2,4-diphosphonoglutaric acid at 20°–120° C., subsequently aspirating the precipitate or subsequently concentrating the aqueous solution.

The novel substances according to the invention of formula I and their salts can be administered in any liquid or solid form suitable for achieving an effective dose e.g. orally, rectally, topically, parenterally, subcutaneously, ocularly, nasally, buccally, intravenously or transdermally. In this case the usual forms of administration come into consideration such as for example tablets, capsules, coated tablets, syrups, solutions, suspensions etc.. Water is preferably used as an injection medium which contains the usual additives for injection solutions such as stabilizing agents, solubilizers and buffers.

Such additives are for example tartrate and citrate buffer, ethanol, complexing agents (such as ethylenediamine tetraacetic acid and their non-toxic salts), high molecular polymers (such as liquid polyethylene oxide) to regulate viscosity. Liquid vehicles for injection solutions must be sterile and are preferably dispensed into ampoules. Solid vehicles are for example starch, lactose, mannitol, methylcellulose, talcum, highly dispersed silicic acids, high molecular fatty acids (such as stearic acid), gelatins, agar-agar, calcium phosphate, magnesium stearate, animal and vegetable fats, solid high molecular polymers (such as polyethylene glycols); suitable preparations for oral administration can, if desired, contain flavourings or sweeteners.

The dosage can depend on various factors such as type of application, species, age and/or individual state. The daily doses to be administered are about 10–1000 mg/person, preferably 100–500 mg/person and can be taken once or divided into several doses.

A pharmaceutical formulation of these 2,4-diphosphonoglutaric acids can also be administered intermittently. Administration over e.g. 1–90 days can for example be followed by a substance-free period of e.g. 30–180 days which can again be followed by administration of the substance over 1–90 days.

In addition to the compounds mentioned in the examples and components which can be derived by combining all meanings for the substituents mentioned in the claims, the following 2,4-diphosphonoglutaric acid derivatives are preferred within the meaning of the invention as well as their sodium, potassium, ammonium, calcium, zinc and magnesium salts, carboxylic acid methyl, ethyl or benzyl esters.

2,4-diphosphono-2-ethyl-glutaric acid
2,4-diphosphono-2-isopropyl-glutaric acid
2,4-diphosphono-2-hexyl-glutaric acid
2,4-diphosphono-2-hydroxymethyl-glutaric acid
2,4-diphosphono-2-(3-hydroxypropyl)-glutaric acid
2,4-diphosphono-2-(4-hydroxybutyl)-glutaric acid
2,4-diphosphono-2-(2-methoxyethyl)-glutaric acid
2,4-diphosphono-2-butoxymethyl-glutaric acid
2,4-diphosphono-2-ethoxymethyl-glutaric acid
2,4-diphosphono-2-(2-aminoethyl)-glutaric acid
2,4-diphosphono-2-(4-aminobutyl)-glutaric acid
2,4-diphosphono-2-(2-N-methyl-N-pentyl-aminoethyl)-glutaric acid
2,4-diphosphono-2-(2-dimethylaminoethyl)-glutaric acid
2,4-diphosphono-2-(2-N-methyl-N-propylaminoethyl)- glutaric acid
2,4-diphosphono-2-methylmercaptomethyl-glutaric acid
2,4-diphosphono-2-methylsulfinylmethyl-glutaric acid
2,4-diphosphono-2-methanesulfonylmethyl-glutaric acid
2,4-diphosphono-2-(2-cyclohexylethyl)-glutaric acid
2,4-diphosphono-2-benzyl-glutaric acid
2,4-diphosphono-2-(2-phenylethyl)-glutaric acid
2,4-diphosphono-2-(4-chlorobenzyl)-glutaric acid
2,4-diphosphono-2-[2-(4-methylphenyl)ethyl]-glutaric acid
2,4-diphosphono-2-(3,4-dichlorobenzyl)-glutaric acid
2,4-diphosphono-2-[2-(5-chloro-2-methoxyphenyl)ethyl]-glutaric acid 2,4-diphosphono-2-[2-(2-pyridyl)ethyl]-glutaric acid
2,4-diphosphono-2-[2-(3-pyridyl)ethyl]-glutaric acid
2,4-diphosphono-2-[2-(4-pyridyl)ethyl]-glutaric acid
2,4-diphosphono-2-(2-thenyl)-glutaric acid
2,4-diphosphono-2-(3-thenyl)-glutaric acid
2,4-diphosphono-2-(2-furfuryl)-glutaric acid
2,4-diphosphono-2-[2-(2-imidazolyl)ethyl]-glutaric acid
2,4-diphosphono-2-(1-imidazolylmethyl)-glutaric acid
2,4-diphosphono-2-(1-pyrrolidinylmethyl)-glutaric acid
2,4-diphosphono-2-(1-piperidinylmethyl)-glutaric acid
2,4-diphosphono-2-(1-morpholinylmethyl)-glutaric acid
2,4-diphosphono-2-allyl-glutaric acid
2,4-diphosphono-2-(but-2-enyl)-glutaric acid
2,4-diphosphono-2-cyclopentyl-glutaric acid
2,4-diphosphono-2-cycloheptyl-glutaric acid
2,4-diphosphono-2-(3-pyridyl)-glutaric acid
2,4-diphosphono-2-(6-methyl-2-pyridyl)-glutaric acid
2,4-diphosphono-2-(5-chloro-2-pyridyl)-glutaric acid
2,4-diphosphono-2-(2-methyl-4-pyridyl)-glutaric acid
2,4-diphosphono-2-(2-furyl)-glutaric acid
2,4-diphosphono-2-(3-thienyl)-glutaric acid
2,4-diphosphono-2-(2-imidazolyl)-glutaric acid
2,4-diphosphono-2-(4-imidazolyl)-glutaric acid
2,4-diphosphono-2-(2-methyl-4-imidazolyl)-glutaric acid
2,4-diphosphono-2-(2-methoxyphenyl)-glutaric acid
2,4-diphosphono-2-(5-chloro-2-methoxyphenyl)-glutaric acid
2,4-diphosphono-2-(3,4-dichlorophenyl)-glutaric acid
2,4-diphosphono-2-(4-isopropoxyphenyl)-glutaric acid
2,4-diphosphono-2-(4-methylphenyl)-glutaric acid
2,4-diphosphono-2-(2,4-dimethylphenyl)-glutaric acid
2,4-diphosphono-2-(3-hydroxyphenyl)-glutaric acid
2,4-diphosphono-2-(4-dimethylaminophenyl)-glutaric acid
2,4-diphosphono-2-(4-N-methyl-N-pentylaminophenyl)-glutaric acid
2,4-diphosphono-2 -(4-methylmercaptophenyl)-glutaric acid
2,4-diphosphono-2 -(4-methylsulfinylphenyl)-glutaric acid
2,4-diphosphono-2 -(4-methylsulfonylphenyl)-glutaric acid
2,4-diphosphono-2 -(4-carboxyphenyl)-glutaric acid
2,4-diphosphono-2 -(4-ethoxycarbonylphenyl)-glutaric acid
2,4-diphosphono-2 -(4-carboxamidophenyl)-glutaric acid
2,4-diphosphono-2 -(4-N,N-dimethylcarboxamidophenyl)-glutaric acid
2,4-diphosphono-2-(3-cyanophenyl)-glutaric acid
2,4-diphosphono-2-(4-cyanophenyl)-glutaric acid
2,4-diphosphono-2-(1-naphthyl)-glutaric acid
2,4-diphosphono-2-(2-naphthyl)-glutaric acid
2,4-diphosphono-2-(3-indolyl)-glutaric acid
2,4-diphosphono-2-(3-indolylmethyl)-glutaric acid
2,4-diphosphono-2-(2,3-dihydroxypropyl)-glutaric acid The following examples show some of the variants of processes which can be used to synthesize the compounds according to the invention. However, they are not intended to represent any limitation of the subject matter of the invention. The structure of the compounds was checked by $^1$H, $^{31}$P and if necessary by $^{13}$C nuclear resonance spectroscopy. The purity of the substances was determined by means of elemental analysis (C,H,N,P if necessary Na) and by thin layer chromatography or by thin layer electrophoresis (cellulose, oxalate buffer pH 4).

EXAMPLE 1

2,4-diphosphono-2-phenyl-glutaric acid

A solution of 9 g α-phosphonophenylacetic acid triethyl ester is added dropwise to a suspension of 0.75 g sodium hydride in 30 ml dry tetrahydrofuran. It is stirred for 30 minutes at room temperature and subsequently 4.9 g 2-phosphonoacrylic acid trimethyl ester is added dropwise to this. The reaction mixture is stirred for 1 hour at 30°–40° C. and finally for a further 2 hours at 60° C. The mixture is evaporated, the residue is taken up in ethyl acetate and the organic phase is extracted by shaking with aqueous ammonium chloride solution. The ethyl acetate phase is dried and evaporated. The crude product (10.5 g) is purified by column chromatography on silica gel using ethyl acetate/isohexane 1:2, ethyl acetate/methanol 95:5 and 80:20. The desired product is present in the ethyl acetate/methanol 8:2 fractions. 4.5 g of an oily 2,4-diphosphono-2-phenylglutaric acid- diethyl-trimethyl ester (mixture of diastereomers) is obtained. The intermediate product obtained in this manner is boiled under reflux for 36 hours with 50 ml 6 N HCl and the reaction mixture is evaporated to dryness. The residue is purified by chromatography on the adsorber resin HP 20SS (Mitsubishi Co.) using water as the eluting agent. Two products are obtained which according to $^1$H-NMR and mass spectroscopy prove to be the R,R/S,S and R,S/S,R diastereomers of 2,4-diphosphono-2-phenyl-glutaric acid.

One obtains:

1.5 g of diastereomer 1 of 2,4-diphosphono-2-phenylglutaric acid $^1$H-NMR (D$_2$O) δ (ppm): 7.5 (m, 5H); 3.05 (m, 3H)

0.6 g of diastereomer 2 of 2,4-diphosphono-2-phenylglutaric acid $^1$H-NMR (D$_2$O) δ (ppm): 7.5 (m, 2H); 6.9 (m, 3H); 3.27 (m, 1H); 2.85 (m, 2H)

EXAMPLE 2

2,4-Diphosphono-2-methyl-glutaric acid is obtained analogously to example 1 as a mixture of diastereomers starting from 2-phosphonopropionic acid triethyl ester.
$^1$H-NMR (D$_2$O): δ (ppm) 2.1–3.1 (m, 3H), 1.4, 1.35 (2d, 3H)

EXAMPLE 3

2,4-Diphosphono-2-butyl-glutaric acid is obtained analogously to example 1 in the form of two products starting from 2-phosphonohexanoic acid triethyl ester which prove to be the R,RS,S and R,SS,R diastereomers according to $^1$H-NMR and mass spectroscopy.
Diastereomer 1
$^1$H-NMR (D$_2$O): δ (ppm) 3.22 (dd, 1H); 2.68 (m, 1H) 2.35 (m, 1H); 1.85 (m, 2H); 1.35 (m, 4H); 0.9 (t, 3H)
Diastereomer 2
$^1$H-NMR (D$_2$O): δ (ppm) 3.35 (dd, 1H); 2.65 (m, 1H) 2.28 (m, 2H); 1.37 (m, 4H); 0.88 (t, 3H)

EXAMPLE 4

2,4-diphosphono-2-pyrrolidinopropylglutaric acid 4.1 2.2 g phosphonoacetic acid triethyl ester is dissolved in 20 ml dimethylformamide and admixed with 240 mg sodium hydride. The mixture is stirred for 30 minutes and then 2.5 g 1-bromo-3-tert.-butyldimethylsilyloxypropan is added. After stirring for 4 hours the reaction mixture is evaporated to dryness, the residue is admixed with ammonium chloride solution and the product is extracted with ether. The crude product is purified by chromatography over silica gel (mobile solvent ethyl acetate/isohexane 2:1). 1.7 g 5-tert. butyldimethylsilyloxy-2-phosphonovaleric acid triethyl ester is obtained.

4.2 The product obtained from 4.1 is reacted analogously to example 1 with 2-phosphonoacrylic acid trimethyl ester.

The acidic saponification of the ester functions is omitted and instead the silyl protecting group is cleaved by the action of 1M HF in acetonitrile. In this way 2,4-diphosphono-2-hydroxypropylglutaric acid triethyltrimethyl ester is obtained.

4.3 The hydroxy compound (1.5 g) obtained from 4.2 is dissolved in 20 ml methylene chloride and reacted with 0.27 ml methanesulfonyl chloride in the presence of 0.55 ml triethylamine while cooling on ice. It is stirred for 30 minutes and the methylene chloride phase is extracted by shaking with sodium bicarbonate solution. After the organic phase has been evaporated to dryness, 1.6 g of the corresponding O-methanesulfonyl compound remains which is admixed with 5 ml pyrrolidine. It is allowed to stand overnight, ether is added and it is filtered. The filtrate is evaporated to dryness. 1.5 g of the corresponding pyrrolidino compound remains which is taken up in 20 ml 6N hydrochloric acid and boiled under reflux for 24 hours. The reaction mixture is extracted with ethyl acetate, the aqueous phase is boiled and evaporated to dryness. The residue is dissolved in water, the solution is neutralized with 1N NaOH (pH 7) and evaporated. The remaining product is stirred with acetone, the precipitate is suction filtered and dried. 1.15 g of the title compound is obtained as the tetrasodium salt (mixture of diastereomers).

$^1$H-NMR (D$_2$O): δ (ppm) 4.3; 4.05 (m, 1H); 3.8 (m, 3H); 3.3 (m, 6H); 2.2 (m, 8H)

EXAMPLE 5

2-Aminobutyl-2,4-diphosphonoglutaric acid 3.7 g 2-bromo-6-phthalimidohexanoic acid ethyl ester is added to 1.9 ml triethylphosphite heated to 145° C. and the mixture is stirred for 4 hours at a bath temperature of 160° C. The excess triethylphosphite is removed by distillation and the residue is chromatographed over silica gel using ethyl acetate. 0.9 g 2-phosphono-6-phthalimidohexanoic acid triethyl ester is obtained which is reacted analogously to example 1 with phosphonoacrylic acid trimethyl ester. The product is also saponified analogously to example 1 by boiling with hydrochloric acid, the phthalic acid which is formed is extracted with ethyl acetate and the product is isolated from the aqueous phase. The tetrasodium salt of 2-aminobutyl-2,4-diphosphonoglutaric acid is obtained as a mixture of diastereomers by neutralizing the aqueous solution to pH 7, evaporating and triturating the residue with acetone.

$^1$H-NMR (D$_2$O): δ (ppm) 4.2, 3.7 (m, 1H); 3.1 (m, 2H); 2.5 (m, 2H); 1.7 (m, 6H)

EXAMPLE 6

Report of pharmacological experiments

Inhibition of non-stimulated bone resorption by determining the excretion of [$^3$H]-tetracycline in urine:

From birth onwards rats received a twice-weekly injection of increasing amounts of a solution of 3.7×10$^5$ Bq/ml (10 μCi/ml) [7-$^3$H]-tetracycline ([$^3$H]TC); New England Nuclear, Boston, Mass.) with a specific activity of 679 mCi/mmol. The volume per injection is increased from 50 μl/week to 250 μl in the fifth week and kept at this level for a further week. The total amount of administered [$^3$H]TC was 20 μCi per rat. 51-day-old rats are transferred to individual metabolic cages and received a group feeding with feed which contained 0.5% Ca and 0.35% P. This feed was produced by addition of appropriate amounts of calcium and phosphate (SODI 2134, "Klingenthalmühle"). The animals received distilled water ad libitum during the entire duration of the experiment. Collection of 24 hour urine was begun after 61 days. The urine was collected daily at 11 o'clock; the animals also received food at this time. On the sixth day after the start of the urine collection, the animals received subcutaneous injections of the substance (at 8 a.m. and 5 p.m.). The inhibition of bone resorption is indicated by reduced [$^3$H]-tetracycline excretion on the eighth day after the start of urine collection. The $^3$H-TC in urine is determined by liquid scintillation by adding 10 ml of the scintillator Pico-Fluor 30 (Packard International, Zurich, Switzerland) to 1 ml of the urine.

$$\% \text{ rel. inhibition} = \frac{[Xcpm_{day5} - (Ccpm_{day8} - Ccpm_{day5})] - Xcpm_{day8}}{[Xcpm_{day5} - (Ccpm_{day8} - Ccpm_{day5})]} \times 100\%$$

$X$ = treated animals
$C$ = control animals

TABLE

| Example No. | % rel. inhibition/dosage |
|---|---|
| 4 | 37% at 2 × 200 mg/kg |
| 5 | 45% at 2 × 200 mg/kg |

We claim:
1. A compound of the formula

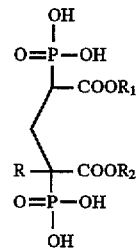

(I)

wherein

R is

C$_1$–C$_6$ alkyl which is unsubstituted or substituted by hydroxy, C$_1$–C$_6$ alkoxy, amino, di-C$_1$–C$_6$ alkylamino, C$_1$–C$_6$alkylmercapto, C$_1$–C$_6$ alkyl sulfinyl, C$_1$–C$_6$ alkansulfonyl, C$_3$–C$_7$ cycloalkyl, phenyl, naphthyl, pyrrolidine, piperidine, azepine, tetrahydrofuran, tetrahydropyran, morpholine, dioxan, furan, thiophene, pyridine, pyrazole, imidazole, thiazole, oxazole, pyrimidine or pyrazine, C$_3$–C$_6$ alkenyl, C$_3$–C$_7$ cycloalkyl, C$_5$–C$_7$ cycloalkenyl, phenyl, naphthyl, pyrrolidine, piperidine, azepine, tetrahydrofuran, tetrahydropyran, morpholine, dioxan, furan, thiophene, pyridine, pyrazole, imidazole, thiazole, oxazole, pyrimidine or pyrazine, wherein heterocyclic rings are unsubstituted or substituted at least once by halogen or lower alkyl or alkoxy, and phenyl or naphthyl rings are unsubstituted or substituted at least once by lower alkyl or alkoxy, halogen, hydroxy, amino, dialkylamino, alkylmercapto, alkylsulfinyl, alkanesulfonyl, carboxyl, alkoxycarbonyl, cyano or carboxamido which can be substituted once or twice by lower alkyl, and R$_1$ and R$_2$ are independently hydrogen, C$_1$–C$_6$ alkyl, C$_3$–C$_7$ cycloalkyl, phenyl, phenylmethyl, naphthyl, or naphthylmethyl, wherein the phenyl or naphthyl ring is unsubstituted or substituted at least once by lower alkyl or alkoxy, halogen, hydroxyl, amino, dialkylamino, alkylmercapto, alkylsulfinyl, carboxyl, alkoxycarbonyl, cyano, alkanesulfonyl, or carboxamido which can be substituted once or twice by lower alkyl, or optically active compounds thereof or pharmacologically acceptable salts thereof.

2. Compound of claim 1, wherein R is a heterocyclic ring, and the heterocyclic ring is pyrrolidine, piperidine, morpholine, furan, thiophene, pyridine or imidazole.

3. A compound of the formula

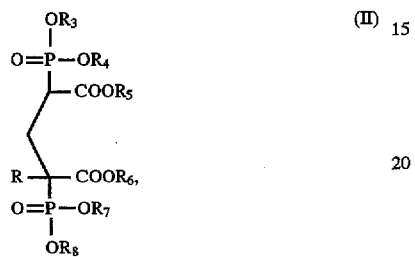 (II)

wherein

R is $C_1$–$C_6$ alkyl which is unsubstituted or substituted by hydroxy, $C_1$–$C_6$ alkoxy, amino, di-$C_1$–$C_6$ alkylamino, $C_1$–$C_6$ alkylmercapto, $C_1$–$C_6$ alkylsulfinyl, $C_1$–$C_6$ alkansulfonyl, $C_3$–$C_7$ cycloalkyl, phenyl, naphthyl, pyrrolidine, piperidine, azepine, tetrahydrofuran, tetrahydropyran, morpholine, dioxan, furan, thiophene, pyridine, pyrazole, imidazole, thiazole, oxazole, pyrimidine or pyrazine, $C_3$–$C_6$ alkenyl, $C_3$–$C_7$ cycloalkyl, $C_5$–$C_7$ cycloalkenyl, phenyl, naphthyl, pyrrolidine, piperidine, azepine, tetrahydrofuran, tetrahydropyran, morpholine, dioxan, furan, thiophene, pyridine, pyrazole, imidazole, thiazole, oxazole, pyrimidine or pyrazine, wherein heterocyclic rings are unsubstituted or substituted at least once by halogen or lower alkyl or alkoxy, and phenyl or naphthyl rings are unsubstituted or substituted at least once by lower alkyl or alkoxy, halogen, hydroxy, amino, dialkylamino, alkylmercapto, alkylsulfinyl, alkanesulfonyl, carboxyl, alkoxycarbonyl, cyano or carboxamido which can be substituted once or twice by lower alkyl, and $R_3$, $R_4$, $R_5$, $R_6$, $R_7$ and $R_8$ are independently $C_1$–$C_6$ alkyl, $C_5$–$C_7$ cycloalkyl, phenyl, naphthyl, phenylmethyl or naphthylmethyl, wherein the phenyl or naphthyl ring is unsubstituted or substituted at least once by lower alkyl, halogen, hydroxy, alkoxy, amino, dialkylamino, alkylmercapto, alkylsulfinyl, carboxyl, alkanesulfonyl or carboxamido which can be substituted once or twice by lower alkyl, or an optically active compound thereof.

4. Pharmaceutical composition suitable for the treatment of calcium metabolism diseases, comprising a calcium metabolism disease treating effective amount of a compound of claim 1 and a pharmaceutically acceptable carrier or diluent.

5. A method of treating a calcium metabolism disease in a patient in need of such treatment, comprising administering to said patient a calcium metabolism disease treating effective amount of a compound of claim 1.

6. Compound of claim 1, wherein the compound is 2,4-diphosphono-2-phenyl-glutaric acid 2,4-diphosphono-2-methyl-glutaric acid 2,4-diphosphono-2-butyl-glutaric acid 2,4-diphosphono-2-pyrrolidinopropylglutaric acid 2-aminobutyl-2,4-diphosphonoglutaric acid.

* * * * *